United States Patent [19]
Gogate et al.

[11] Patent Number: 5,808,148
[45] Date of Patent: Sep. 15, 1998

[54] PREPARATION OF α,β-UNSATURATED CARBOXYLIC ACIDS AND ESTERS

[75] Inventors: Makarand Ratnakar Gogate, Durham; James Jerry Spivey, Cary, both of N.C.; Joseph Robert Zoeller, Kingsport, Tenn.

[73] Assignee: Eastman Chemical Company, Kingsport, Tenn.

[21] Appl. No.: 775,935

[22] Filed: Jan. 3, 1997

[51] Int. Cl.⁶ .................................................. C07C 51/00
[52] U.S. Cl. .......................... 562/599; 562/495; 562/510
[58] Field of Search .................................. 562/599, 495, 562/510

[56] References Cited

U.S. PATENT DOCUMENTS

| | | |
|---|---|---|
| 3,440,276 | 4/1969 | Wolf et al. . |
| 3,535,371 | 10/1970 | Wolf et al. . |
| 3,812,176 | 5/1974 | Lapporte et al. ........................ 260/494 |
| 3,927,078 | 12/1975 | Lapporte et al. ........................ 260/494 |
| 4,085,143 | 4/1978 | Holmes ..................... 260/515 |

OTHER PUBLICATIONS

M. Ai, *J. Catal.*, 107, 201 (1987).
M. Ai, *J. Catal.*, 124, 293 (1990).
M. Ai, *Appl. Catal.*, 36, 221 (1988).
M. Ai, *Appl. Catal.*, 63, 365 (1990).
M. Ai, *Bull, Chem. Soc. Jap.*, 63, 1217 (1990).
M. Ai, *Bull. Chem. Soc. Jap.*, 63, 3722 (1990).
M. Ai, *Appl. Catal.*, 48, 51 (1989, primarily catalyst preparation).
M. Ai, *J. Catal.*, 113, 562 (1988, primarily catalyst preparation).
CA, XP002057753—Abstract 96:7111.
CA 99:175185 (1983).

*Primary Examiner*—Paul J. Killos
*Attorney, Agent, or Firm*—Michael J. Blake; J. Frederick Thomsen; Harry J. Gwinnell

[57] ABSTRACT

Disclosed is a process for the preparation of α,β-unsaturated carboxylic acids and esters thereof which comprises contacting formaldehyde or a source of formaldehyde with a carboxylic acid, ester or anhydride in the presence of a catalyst comprising an oxide of niobium.

4 Claims, No Drawings

PREPARATION OF α,β-UNSATURATED CARBOXYLIC ACIDS AND ESTERS

This invention was made with Government Support under DOE Contract No. DE-AC22-94PC94065 awarded by the Department of Energy. The Government has certain rights in this invention.

This invention pertains to a process for the preparation of α,β-unsaturated carboxylic acids and esters by the condensation of formaldehyde with aliphatic carboxylic acids, esters and anhydrides. More specifically, this invention pertains to the synthesis of α,β-unsaturated carboxylic acids and esters by the condensation of formaldehyde with aliphatic carboxylic acids, esters and anhydrides in the presence of a catalyst comprising oxides of niobium, preferably supported on oxides, including mixed oxides, of silicon, titanium, and/or aluminum.

α, β-Unsaturated acids, particularly acrylic and methacrylic acid, and their ester derivatives are among the most useful organic compounds in the chemical industry wherein their polymerization products find a myriad of applications including plastic sheeting for signs, coatings (including latex paints), adhesives, fibers, and synthetic resins. Given their utility, it would be useful to find alternative processes for the generation of these materials. This is particularly true for the generation of methacrylic acid and its derivatives since the process presently used for the generation of methacrylic acid produces copious quantities of waste and, therefore, represents a challenge to the environment.

The prior art contains numerous references to the condensation of formaldehyde with carboxylic acids and alkyl carboxylate esters according to the equation:

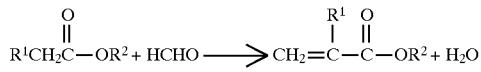

wherein $R^1$ and $R^2$ independently are selected from hydrogen, alkyl and aryl. The condensation of carboxylic acids or esters with formaldehyde over unsupported catalysts consisting of mixed oxides of V and P is described by M. Ai, *J. Catal.*, 107, 201 (1987); M. Ai, *J. Catal.*, 124, 293 (1990); M. Ai, *Appl. Catal.*, 36, 221 (1988); M. Ai, *Shokubai*, 29, 522 (1987); and M. So, JP 01068336 A2. The condensation of carboxylic acids or esters with formaldehyde over catalysts consisting of mixed oxides of V and P on oxides of silicon is described by M. Ai, *Appl. Catal.*, 63, 29 (1990); M. Ai, *Bull. Chem. Soc. Jap.*, 63, 1217 (1990); and M. Ai, *Bull. Chem. Soc. Jap.*, 63, 3722 (1990). The same condensation in the presence of catalysts consisting of mixed oxides of V and P on oxides of titanium is disclosed by M. Ai, *Studies in Surface Sci. and Catal.*, 72, 101 (1992); M. Ai, *Appl. Catal.*, 54, 29 (1989); M. Ai, *Proc. - Int. Congr. Catal.*, 9th (1988) Vol. 4, 1562; M. Ai, *Appl. Catal.*, 48, 51 (1989, primarily catalyst preparation); M. Ai, *J. Catal.*, 113, 562 (1988, primarily catalyst preparation); M. Ai, *Shokubai*, 30, 420 (1988); M. So, JP 01068334; and M. So, JP 01068337. The condensation of propionic acid and formaldehyde in the presence of other catalysts, e.g., alkali metals supported on oxides of silica, is described by O. H. Bailey, R. A. Montag, and J. S. Yoo. *Appl. Catal. A*, 88, 163 (1992); J. S. Yoo. *Appl. Catal. A.*, 102, 215 (1993); A. J. C. Pearson, British Patent 1,428,777 (1976); and Y. Yamamoto, H. Ebata, and K. Kida. *Jpn. Kokai*, 63–115 844 (1988).

It is known (see, for example, Holmes, U.S. Pat. No. 4,085,143 and Toland and Lapporte, U.S. Pat. Nos. 3,927,078 and 3,812,176) that the interaction of anhydrides with aliphatic aldehydes, including formaldehyde, generally leads not to condensation, but to the formation of 1,1-dicarboxylates, at least in the condensed phase, according to Equation (3):

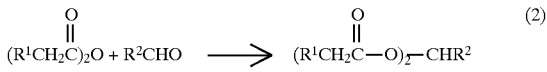

As a consequence, the condensation of aldehydes and anhydrides has seen limited application outside of the well documented condensation with aromatic aldehydes which do not form the diesters readily. (The condensation of anhydrides with aromatic aldehydes is known as the Perkin reaction.) Despite the potential advantages offered by the synthesis of α,β-unsaturated carboxylic acids and anhydrides thereof by the condensation of formaldehyde with aliphatic carboxylic anhydrides, prior art descriptions of such condensations have been limited to U.S. Pat. No. 4,085,143 and S. Oda, T. Nakano, R. Han, JP 06048977 A2.

It is also known that carboxylic acids can react to form ketones according to Equation (3):

This undesired side reaction generally limits the utility of the carboxylic acid/formaldehyde reaction using many of the prior art catalysts, particularly those selected from the group of alkali and alkaline earth metals. The supported group 5 metal (vanadium group, V, Nb, Ta) catalysts all are distinguished from other condensation catalysts by their low ketone generation rates.

We have discovered that catalysts comprising an oxide of niobium such as niobium oxide (niobium pentoxide, $Nb_2O_5$) give improved results such as improved conversions and selectivities when used to catalyze the condensation of aliphatic carboxylic acids, ester and anhydrides with formaldehyde. The improved conversion rates provided by the catalysts utilized in the present invention do not result in the formation of increased amount of ketones according to Equation (3). The present invention therefore provides a process for the preparation of α,β-unsaturated carboxylic acids and esters by the condensation of formaldehyde with aliphatic carboxylic acids, esters and anhydrides in the presence of a catalyst comprising an oxide of niobium. The niobium catalyst preferably is employed in the form of an oxide of niobium supported on an oxide, including mixed oxides, of silicon, titanium, and/or aluminum.

Our novel process involves the reactions:

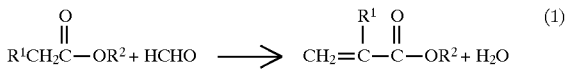

and

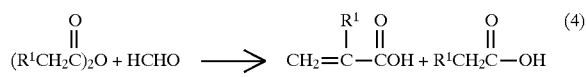

wherein $R^1$ and $R^2$ independently are selected from hydrogen, alkyl and aryl, including substituted alkyl and aryl. The use of carboxylic acid anhydrides in the condensation reaction may be advantageous. As shown by Equation (1), the condensation of formaldehyde with a carboxylic acid or ester produces an equivalent of water. The water produced may inhibit further reaction of additional carboxylic acid and formaldehyde and, in the case of ester feedstocks, also will cause hydrolysis of the ester. When the process is operated using the acid anhydride, water is consumed in a subsequent reaction to form free acid, with the overall condensation reaction represented by Equation (3). The product α,β-unsaturated acid may be separated from the parent acid and the coproduced acid may be used to regenerate the corresponding carboxylic acid anhydride by any of the several known processes. See, for example, the processes disclosed by Cook, "Acetic Anhydride", Chap. 9 in V. H. Agreda and J. R. Zoeller, eds. *Acetic Acid and Its Derivatives*, Marcel Dekker, Inc., New York, N.Y. (USA) (1993), p. 145, and, for the generation of propionic anhydride from propionic acid, ethylene, and carbon monoxide, see U.S. Pat. Nos. 2,658,075, 2,497,304, 3,989,751, 2,593,440, 4,335,058 and 4,483,803.

The catalyst utilized in the process of the present invention comprise an oxide of niobium, preferably supported on an additional oxide selected from common catalyst supports, such as silica, alumina, and titania. The supported catalysts may comprise from about 0.1 to 75 weight percent niobium [Nb] although niobium loadings in the range of about 1 to 30 weight percent are more common. Examples of suitable catalyst support materials include silica, alumina, titania and mixtures thereof. The preferred catalysts comprise about 15 to 25 weight percent niobium oxide on silica. The supported, niobium-based catalysts may be prepared according to known impregnation techniques.

The carboxylic acids, esters and anhydride reactants which may be used in the present invention have the general formulae:

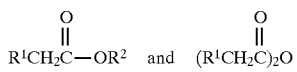

wherein $R^1$ and $R^2$ are independently selected from hydrogen, alkyl of up to about 20 carbon atoms, alkenyl of up to about 20 carbon atoms, or aryl including alkyl substituted aryl of 6 to 10 carbon atoms, e.g., phenyl, tolyl, xylyl, naphthyl, etc. The reactants of particular interest are acetic and propionic acids and the anhydrides thereof.

The formaldehyde reactant may be provided in a variety of forms, although solutions which are reactive with carboxylic acid anhydrides, such as the commonly available aqueous and methanolic solutions, obviously are deleterious to the process when using a carboxylic anhydride as a feedstock. Therefore, the formaldehyde reactant preferably is provided as gaseous formaldehyde, trioxane, or paraformaldehyde. Although the formaldehyde may be added in excess, it is operationally preferable to add the carboxylic acid, ester or anhydride in excess of the formaldehyde. The mole ratio of carboxylic acid, ester or anhydride to formaldehyde (or formaldehyde equivalent) can range from about 1:1 to 50:1 with the preferred range being about 2:1 to 15:1.

Although it is possible to operate the process in the liquid phase, for example by utilizing superatmospheric pressures, we prefer to carry out the process in the vapor phase wherein the reactants are vaporized prior to contact with the catalyst. The vapor can be added with or without a non-reactive (inert) diluent gas such as nitrogen, methane, helium, argon, etc. However, the use of such a nonreactive diluent gas does not provide any advantage to the operation of the process. The gaseous flow rates used in the practice of the process may be varied widely and are a matter of empirical optimization for each combination of catalyst and carboxylic acid, ester and/or anhydride. The gas flow rate typically will be in the range of about 10 to 10,000 liters per kilogram catalyst per hour with a range of about 100 to 1000 L/kg catalyst-hour being preferred.

The process may be operated over a wide range of temperatures and pressures. However, since operation preferably is in the vapor phase, the pressure and temperature chosen should be sufficient to operate above the dew point which is a function of the carboxylic acid, ester or anhydride chosen, the pressure, the temperature, and, if a nonreactive, diluent or carrier gas is used, the concentration of the carboxylic acid, ester or anhydride in the carrier gas. This mode of operation still permits a wide range of conditions but, in general, will require a temperature of about 100° to 650° C., the preferred range being about 200° to 350° C. Reaction pressure may be in the range of about 0.1 to 50 bars absolute with a range of about 0.5 to 5 bars absolute being preferred. The process normally is operated under substantially anhydrous conditions, meaning that no extraneous water is added during the operation of the process. Water, of course, is coproduced in the condensation and the feed materials may contain minor amounts, e.g., up to 500 ppm, water as impurity.

The process of the present invention and the preparation of catalyst used therein are further illustrated by the following examples.

CATALYST PREPARATION

Catalysts comprising niobium on silica, vanadium on silica and tantalum on silica and having metal (Nb, V, Ta) to silicon atomic ratios of 1:99, 5:95, 10:90, and 20:80 were prepared using calculated amounts of metal precursor compounds $NH_4VO_3$, $NbF_5$, and $TaF_5$. The precursor compound was added slowly to a preweighed silica solution (36 percent silica in water, NALCO colloidal silica 1034-A). The resulting solution was then heated gradually, with stirring, to drive off water. The mixtures were calcined at 300° C. for 4 hours followed by calcination at 450° C. for 6 hours. Catalysts obtained were crushed and screened to a 16 to 25 mesh size (0.707 to 1.19 mm for testing) and a <16 mesh size (<1.19 mm) for characterization. The exact precursor compounds required each catalyst synthesis were computed as follows: a 30-g catalyst batch was prepared, of each of the five $V_2O_5/SiO_2$ (1, 5, 10, and 20 percent catalysts). The amounts (g) of starting materials are summarized in Table 1. The amounts of $SiO_2$ refer to amounts of a 36 weight percent aqueous, silica dispersion. A 23.5-g catalyst batch was prepared for the $Nb_2O_5/SiO_2$ catalysts, and an 18.5-g catalyst batch was prepared for the $Ta_2O_5/SiO_2$ catalyst.

TABLE 1

Starting Materials for Catalyst Preparation

| Metal:Si Atomic Ratio | $NH_4VO_3$—$SiO_2$ | $NbF_5$—$SiO_2$ | $TaF_5$—$SiO_2$ |
|---|---|---|---|
| 1:99 | 0.58–81.5 | 0.74–63.8 | 0.84–49.5 |
| 2:98 | 1.15–79.7 | 1.46–62.5 | 1.64–47.8 |
| 5:95 | 2.78–77.3 | 3.53–60.5 | 3.82–46.3 |
| 10:90 | 5.26–70.7 | 6.68–55.4 | 6.84–40.8 |
| 20:80 | 9.49–53.7 | 12.07–42.03 | 11.29–26.77 |

The BET surface area (BET SA, square meters per g), surface acidity (μmol ammonia per g) and q-ratio of some of the above-described niobium-based catalysts are set forth in Table 2. The surface area of the catalysts were measured using a 3-point BET—$N_2$. The BET method for determining specific surface area is described in detail in Brunauer, S., Emmett, P. H., and Teller, E., J. Am. Chem. Soc., 60, 309–316 (1938). The surface acidity is measured by an Altamira catalyst characterization instrument (AMI-100), using ammonia-temperature-programmed desorption (TPD), and a 10 percent ammonia in nitrogen as the probe gas. The q-ratio is defined as the fraction of the ammonia- TPD area between 50° and 300° C. compared to the total area.

TABLE 2

| Nb—Si Atomic Ratio | BET SA | Surface Acidity | q-ratio |
|---|---|---|---|
| 1:99 (1%) | 110.9 | 14.9 | 0.763 |
| 5:95 (5%) | 119.1 | 28.6 | 0.801 |
| 10:90 (10%) | 86.5 | 27.3 | 0.806 |
| 20:80 (20%) | — | 34.8 | 0.746 |

For comparison, a catalyst having a V:Si:P atomic ratio of 1:12:2.8 has a BET SA of 96.5, a Surface Acidity of 150.8 and a q-ratio of 0.444. This V:Si:P catalyst was prepared by adding (i) a solution of 23.4 g $NH_4VO_3$ in 100 mL of hot water containing 20 mL of lactic acid and (ii) a solution of 64.4 g of 85% $H_3PO_4$ in 100 mL hot water to 480 mL of colloidal silica consisting of 30 weight percent silica in water (DuPont Ludox® SM-30). The mixture was stirred at 50° C. to evaporate water and the cake obtained was dried in an oven in which the temperature was increased from 50° C. to 200° C. at the rate of 1° C. per minute. The resulting solid was crushed and a portion having a 8–20 mesh particle size (2.8–0.2 mm) was calcined in air first at 350° C. for 6 hours and then at 450° C. for 6 hours. The catalyst obtained consisted of vanadium, silicon and phosphorus in a V:Si:P atomic ratio of 1:12:2.8.

INVENTION EXAMPLES

The examples described below were carried out in a microreactor consisting of (1) a 40.6 cm (16 inch) section of 316 stainless steel tubing having an inside diameter of 1.25 cm (0.5 inch) which functioned as a preheater and (2) a 35.6 cm (14 inch) section of 316 stainless steel tubing having an inside diameter of 1.25 cm (0.5 inch) which served as the reactor. The preheater was filled with quartz beads and the catalyst was placed in the reactor. The space remaining in the reactor was filled with quartz beads and the beads and catalyst were held in place by the insertion of quartz wool in the reactor tube. The preheater and reactor tube were aligned horizontally, connected by short, well-insulated, stainless steel tubing, and each section placed in a separate electric furnace. A thermocouple was positioned in the catalyst bed. To the inlet of the preheater was connected a nitrogen feed line and a liquid feed line. The exit port of the reactor was connected to a condenser and liquid samples were collected after condensation. The gas outlet of the reactor system was connected to an outlet and an on-line gas chromatograph.

The microreactor was operated by heating the preheater to 300° C. and introducing a continuous nitrogen purge of 220 millimoles per hour (mmol/hour) through the system with the pressure maintained at about 3 bars absolute. Using the thermocouple in the reactor section as a thermostat, the reactor tube then was heated to and maintained at 300° C. throughout the reaction.

A solution of 2 g (0.022 mol) of 1,3,5-trioxane (formaldehyde trimer) in 23 g (0.311 mol) of propionic acid (propionic acid:formaldehyde molar ratio of 4.6:1) was introduced to the preheater at a rate of about 6 g per hour (72.2 mmol/hour propionic acid, 15.5 mmol/hour formaldehyde) via the liquid feed line. This combination results in a nominal gas feed rate of 1080 L/Kg catalyst-hour. The duration of each experiment was 2.58 hours.

The 300° C. preheater temperature is sufficient to both vaporize the propionic acid and convert the trioxane to gaseous monomeric formaldehyde. The vaporized components are swept to, and through, the reactor tube by the nitrogen purge. After passage through the reactor tube the liquid components are condensed, weighed, and analyzed by GC for diethyl ketone, propionic acid, propionic anhydride, methacrylic acid, and methacrylic anhydride. (The last component is generally minor.) The gaseous effluent is analyzed periodically for CO and $CO_2$. For gas analysis, a fixed-volume loop injection onto a Poropak T/molecular sieve 5 Å and a column isolation sequence in conjunction with a thermal conductivity detector (TCD) were used. For liquid analysis, a fused silica capillary column with a 1-mm film thickness of DB was used, with a flame ionization detector (FID).

EXAMPLE 1–4

Four experiments were carried out using the above-described procedure and 5 g of one of the following niobium-based catalysts prepared as described above: Catalyst I having a Nb:Si atomic ratio of 1:99, Catalyst II having a Nb:Si atomic ratio of 5:95, Catalyst III having a Nb:Si atomic ratio of 10:90, and Catalyst IV having a Nb:Si atomic ratio of 20:80. Table 3 shows the catalyst (Cat) used in each example, the total amounts (mmol) of propionic acid (PrOH) and formaldehyde (HCHO) fed to the reactor during each example and total amounts (mmol) of propionic acid, methacrylic acid (MAA) and diethyl ketone (DEK) present in the reactor product effluent.

TABLE 3

| | | Reactor Feeds | | Product Analysis | | |
|---|---|---|---|---|---|---|
| Example | Cat | PrOH | HCHO | PrOH | MAA | DEK |
| 1 | I | 186 | 40 | 176 | 9.2 | 0.20 |
| 2 | II | 186 | 40 | 159 | 23.3 | 0.21 |
| 3 | III | 186 | 40 | 159 | 23.5 | 0.28 |
| 4 | IV | 186 | 40 | 154 | 28.4 | 0.38 |

COMPARATIVE EXAMPLES 1–3

Three additional experiments, each of a duration of 2.58 hours, were carried out using the above-described procedure and 5 g of each of a catalyst having a Ta:Si atomic ratio of 20:80 (Catalyst V), a catalyst having a V:Si atomic ratio of 20:80 (Catalyst VI) and a vanadium-silicon-phosphorus catalyst having a V:Si:P atomic ratio of 1:12:2.8 (Catalyst VII). These catalysts were prepared as described hereinabove. Table 4 shows the catalyst (Cat) used in each comparative example, the total amounts (mmol) of propionic acid (PrOH) and formaldehyde (HCHO) fed to the reactor during each example and total amounts (mmol) of propionic acid, methacrylic acid (MAA) and diethyl ketone (DEK) present in the reactor product effluent. The results obtained in prior Example 4 are included in Table 4 for comparison.

TABLE 4

| | | Reactor Feeds | | Product Analysis | | |
|---|---|---|---|---|---|---|
| Example | Cat | PrOH | HCHO | PrOH | MAA | DEK |
| C-1 | V | 186 | 40 | 175 | 10.4 | 0.21 |
| C-2 | VI | 186 | 40 | 180 | 5.6 | 0.17 |
| C-3 | VII | 186 | 40 | 166 | 18.8 | 0.25 |
| 4 | IV | 186 | 40 | 154 | 28.4 | 0.38 |

The data presented in Table 4 clearly shows the superiority of a niobium-based catalyst on the rate of methacrylic acid production.

The invention has been described in detail with particular reference to preferred embodiments thereof, but it will be understood that variations and modifications can be effected within the spirit and scope of the invention.

We claim:

1. Process for the preparation of an α,β-unsaturated carboxylic acid which comprises contacting formaldehyde or a source of formaldehyde with a carboxylic acid or a carboxylic acid anhydride in the presence of a catalyst comprising an oxide of niobium.

2. Process according to claim 1 for the preparation of an α,β-unsaturated carboxylic acid having the formula

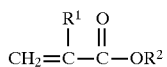

which comprises contacting formaldehyde or a source of formaldehyde with a carboxylic acid having the formula

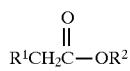

or with a carboxylic acid anhydride having the formula

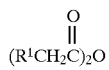

at a temperature of 100° to 650° C. in the presence of a catalyst comprising an oxide of niobium and wherein $R^1$ is selected from hydrogen, alkyl of up to about 20 carbon atoms, alkenyl of up to about 20 carbon atoms, or aryl of 6 to 10 carbon atoms and $R^2$ is hydrogen.

3. Process for the preparation of an α,β-unsaturated carboxylic acid having the formula

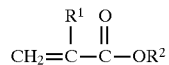

which comprises contacting in the gas phase formaldehyde or a source of formaldehyde with a carboxylic acid having the formula

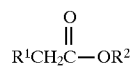

or with a carboxylic acid anhydride having the formula

at a temperature of 200° to 350° C. in the presence of a catalyst comprising an oxide of niobium supported on silica, alumina or titania wherein the weight percent niobium is in the range of about 1 to 30 weight percent and wherein $R^1$ is hydrogen or methyl and $R^2$ is hydrogen.

4. Process according to claim 3 wherein the catalyst comprises an oxide of niobium supported on silica wherein the weight percent niobium is in the range of about 15 to 25 weight percent.

* * * * *